United States Patent [19]

Weissmüller et al.

[11] Patent Number: 4,615,725
[45] Date of Patent: Oct. 7, 1986

[54] TETRAHYDROFURAN-2-YLMETHYLAMINES AND FUNGICIDAL AND PLANT GROWTH REGULATING USE

[75] Inventors: Joachim Weissmüller; Wolfgang Krämer; Dieter Berg, all of Wuppertal; Paul Reinecke, Leverkusen; Wilhelm Brandes, Leichlingen; Gerd Hänssler, Leverkusen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 720,827

[22] Filed: Apr. 8, 1985

[30] Foreign Application Priority Data

Apr. 13, 1984 [DE] Fed. Rep. of Germany ....... 3413996

[51] Int. Cl.$^4$ ..................... A01N 43/08; A01N 43/40; C07D 307/14; C07D 405/06
[52] U.S. Cl. .......................................... 71/88; 71/92; 71/94; 71/95; 514/212; 514/227; 514/232; 514/236; 514/237; 514/240; 514/255; 514/326; 514/422; 514/471; 546/214; 548/517; 549/492; 549/494; 549/495; 540/596
[58] Field of Search ....................... 549/492, 494, 495; 260/330.9; 544/152, 374; 546/214; 548/517; 71/88, 92, 94, 95; 514/212, 227, 232, 236, 237, 240, 255, 326, 422, 471

[56] References Cited

FOREIGN PATENT DOCUMENTS 3140633 4/1983 Fed. Rep. of Germany .
3305769 12/1983 Fed. Rep. of Germany .
77877 5/1983 Japan .
907528 10/1965 United Kingdom .

OTHER PUBLICATIONS

Mndzhoyan et al, Chemical Abstracts, vol. 57 (1962) 11137c.
Knasnyuk-Mudryi et al, Chemical Abstracts, vol. 77 (1972) 48114g.

Primary Examiner—Richard L. Raymond
Attorney, Agent, or Firm—Sprung Horn Kramer & Woods

[57] ABSTRACT

Tetrahydrofuran-2-ylmethylamines of the formula

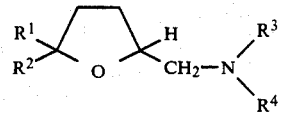

in which
 $R^1$ represents optionally substituted naphthyl, optionally substituted cycloalkyl or cycloalkenyl, optionally substituted phenyl, or alkyl which is substituted by in each case optionally substituted phenyl, phenoxy or phenylthio,
 $R^2$ represents hydrogen or methyl,
 $R^3$ represents alkyl and
 $R^4$ represents alkyl, alkenyl, alkinyl or optionally substituted aralkyl, or
 $R^3$ and $R^4$, together with the nitrogen atom to which they are bonded, represent an optionally substituted heterocyclic radical, which can contain further hetero-atoms, excluding the compounds in which $R^3$ and $R^4$ both represent methyl, $R^1$ represents unsubstituted phenyl and $R^2$ at the same time represents hydrogen, or plant-tolerated addition products thereof with acids or metal salts, which possess fungicidal and plant growth regulating activities.

13 Claims, No Drawings

TETRAHYDROFURAN-2-YLMETHYLAMINES AND FUNGICIDAL AND PLANT GROWTH REGULATING USE

The invention relates to new tetrahydrofuran-2-ylmethylamines, a process for their preparation and their use as plant protection agents, in particular as fungicides and plant growth regulators.

It is already known that certain 1,3-dioxolan-4-yl-methylamines, such as, for example, 2-[1-(3-chlorophenoxy)-2-methylprop-2-yl]-2-methyl-4-(3-methylpiperidin-1-ylmethyl)-1,3-dioxolane, 2-[1-(2,4-dichlorophenoxy)-2-methylprop-2-yl]-2-methyl-4-(3-methylpiperidin-1-ylmethyl)-1,3-dioxolane or 2-[1-(2,4-dichlorophenoxy)-2-methylprop-2-yl]-2-methyl-4-(3,5-dimethylpiperidin-1-ylmethyl)-1,3-dioxolane, have fungicidal properties (compare, for example, DE-OS (German Published Specification) No. 3,305,769).

However, the fungicidal properties of these 1,3-dioxolan-4-ylmethylamines which are already known may not always be completely satisfactory in all fields of use, especially when low amounts are applied and the concentrations are low.

New tetrahydrofuran-2-ylmethylamines of the general formula (I)

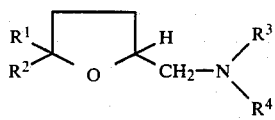

(I)

in which
R$^1$ represents optionally substituted naphthyl, optionally substituted cycloalkyl or cycloalkenyl, optionally substituted phenyl, or alkyl which is substituted by in each case optionally substituted phenyl, phenoxy or phenylthio,
R$^2$ represents hydrogen or methyl,
R$^3$ represents alkyl and
R$^4$ represents alkyl, alkenyl, alkinyl or optionally substituted aralkyl, or
R$^3$ and R$^4$, together with the nitrogen atom to which they are bonded, represent an optionally substituted heterocyclic radical, which can contain further hetero-atoms,
excluding the compounds in which R$^3$ and R$^4$ both represent methyl, R$^1$ represents unsubstituted phenyl and R$^2$ at the same time represents hydrogen, and acid addition salts and metal salt complexes thereof which are tolerated by plants, have been found.

The compounds of the formula (I) can be obtained as geometric and/or optical isomers or isomer mixtures of varying composition. Both the pure isomers and the isomer mixtures are claimed according to the invention.

It has furthermore been found that the new tetrahydrofuran-2-ylmethylamines of the general formula (I)

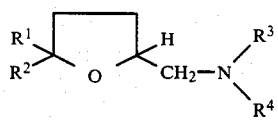

(I)

in which
R$^1$ represents optionally substituted naphthyl, optionally substituted cycloalkyl or cycloalkenyl, optionally substituted phenyl, or alkyl which is substituted by in each case optionally substituted phenyl, phenoxy or phenylthio,
R$^2$ represents hydrogen or methyl,
R$^3$ represents alkyl and
R$^4$ represents alkyl, alkenyl, alkinyl or optionally substituted aralkyl, or
R$^3$ and R$^4$, together with the nitrogen atom to which they are bonded, represent an optionally substituted heterocyclic radical, which can contain further hetero-atoms,
excluding the compounds in which R$^3$ and R$^4$ both represent methyl, R$^1$ represent unsubstituted phenyl and R$^2$ at the same time represents hydrogen, and acid addition salts and metal salt complexes thereof which are tolerated by plants, are obtained by a process in which tetrahydrofuran derivatives of the formula (II)

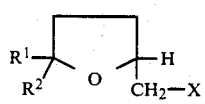

(II)

in which
R$^1$ and R$^2$ have the abovementioned meaning and
X represents an electron-withdrawing leaving grouping,
are reacted with amines of the general formula (III)

(III)

in which
R$^3$ and R$^4$ have the abovementioned meaning, if appropriate in the presence of a diluent, if appropriate in the presence of a catalyst and if appropriate in the presence of an acid-binding agent, and, if appropriate, an acid or a metal salt is then added on.

It is also possible to quaternise the tetrahydrofuran-2-ylmethylamines of the formula (I) according to the invention on the nitrogen by generally customary methods to give the corresponding tetra-substituted ammonium salts.

Finally, it has been found that the new tetrahydrofuran-2-ylmethylamines of the general formula (I) have fungicidal and plant growth-regulating properties.

Surprisingly, the tetrahydrofuran-2-ylmethylamines of the formula (I) according to the invention exhibit a more powerful fungicidal activity than the 1,3-dioxolan-4-ylmethylamines which are known from the prior art, such as, for example, 2-[1-(3-chlorophenoxy)-2-methylprop-2-yl]-2-methyl-4-(3-methylpiperidin-1-ylmethyl)-1,3-dioxolane, 2-[1-(2,4-dichlorophenoxy)-2-methylprop-2-yl]-2-methyl-4-(3-methylpiperidin-1-ylmethyl)-1,3-dioxolane or 2-[1-(2,4-dichlorophenoxy)-2-methylprop-2-yl]-2-methyl-4-(3,5-dimethylpiperidin-1-ylmethyl)-1,3-dioxolane, which are closely related compounds chemically and from the point of view of their action.

Formula (I) provides a general definition of the tetrahydrofuran-2-ylmethylamines according to the invention. Preferred compounds of the formula (I) are those in which
R$^1$ represents naphthyl which is optionally monosubstituted or polysubstituted by identical or different substituents, possible substituents being: hydroxyl, halogen or in each case straight-chain or branched alkyl, alkoxy, alkenyloxy, alkinyloxy or alkanoyloxy with in each case up to 4 carbon atoms in the alkyl part; or represents cycloalkyl or cycloalkenyl with in each case 3 to 7 carbon atoms and in each case optionally monosubstituted or polysubstituted by identical or different straight-chain or branched alkyl radicals with 1 to 4 carbon atoms; or represents phenyl which is optionally monosubstituted or polysubstituted by identical or different substituents or represents phenylalkyl, phenoxyalkyl or phenylthioalkyl with in each case up to 8 carbon atoms in the straight-chain or branched alkyl part, optionally monosubstituted or polysubstituted in the phenyl nucleus by identical or different substituents, possible substituents on the phenyl in each case being: hydroxyl, halogen, cyano, nitro, in each case straight-chain or branched alkyl, alkoxy, alkenyloxy, alkinyloxy or alkylthio with in each case up to 4 carbon atoms, halogenalkyl, halogenoalkoxy or halogenoalkylthio with in each case 1 or 2 carbon atoms and 1 to 5 identical or different halogen atoms, cycloalkyl with 5 to 7 carbon atoms, straight-chain or branched alkoxycarbonyl or alkanoyloxy with in each case up to 4 carbon atoms in the alkyl part, phenyl or phenoxy, optionally substituted by halogen, in particular fluorine or chlorine, or by straight-chain or branched alkyl with 1 to 4 carbon atoms, or the radical R—O—N=CH—, wherein R in each case represents straight-chain or branched alkyl, alkenyl or alkinyl with up to 4 carbon atoms;

$R^2$ represents hydrogen or methyl, $R^3$ represents straight-chain or branched alkyl with 1 to 4 carbon atoms and $R^4$ represents straight-chain or branched alkyl with 1 to 6 carbon atoms, or represents straight-chain or branched alkenyl or alkinyl with in each case up to 6 carbon atoms, or represents aralkyl which has 1 or 2 carbon atoms in the alkyl part and 6 to 10 carbon atoms in the aryl part and is optionally monosubstituted or polysubstituted by identical or different substituents, possible substituents on the aryl in each case being: halogen, straight-chain or branched alkyl with 1 to 4 carbon atoms or halogenoalkyl with 1 or 2 carbon atoms and 3 to 5 identical or different halogen atoms, or $R^3$ and $R^4$, together with the nitrogen atom to which they are bonded, represent a 5-membered to 7-membered saturated heterocyclic radical which has 1 to 3 hetero-atoms, preferably nitrogen and oxygen, and is optionally monosubstituted or polysubstituted by identical or different substituents, possible substituents being: straight-chain or branched alkyl with 1 to 4 carbon atoms, straight-chain or branched alkoxycarbonyl with up to 5 carbon atoms, phenyl, hydroxymethyl or the R'—CO—O—CH$_2$ group, wherein R' represent straight-chain or branched alkyl, alkoxy or alkylamino or dialkylamino with in each case 1 to 6 carbon atoms in the individual alkyl part, or represents straight-chain or branched alkoxyalkyl with in each case 1 to 6 carbon atoms in the two alkyl parts, but wherein $R^3$ and $R^4$ do not both represent methyl if $R^1$ represents unsubstituted phenyl and at the same time $R^2$ represents hydrogen.

Particularly preferred compounds of the general formula (I) are those in which $R^1$ represents naphthyl which is optionally mono-, di- or tri-substituted by identical or different substituents, possible substituents being: fluorine, chlorine, bromine, hydroxyl, methyl, ethyl, methoxy, ethoxy, allyloxy, propargyloxy and acetyloxy; or represents cycloalkyl or cycloalkenyl with 5 to 7 carbon atoms and in each case optionally mono-, di- or tri-substituted by identical or different substituents from the group comprising methyl and ethyl, or represents phenyl which is optionally mono-, di- or tri-substituted by identical or different substituents; or represents a radical of the formula

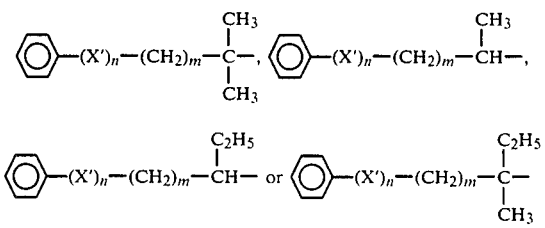

which is optionally mono-, di- or tri-substituted in the phenyl nucleus by identical or different substituents, possible substituents from the phenyl in each case being: hydroxyl, fluorine, chlorine, bromine, cyano, nitro, methyl, methoxy, methylthio, ethyl, ethoxy, ethylthio, n- and i-propyl, isopropyloxy, n-, i-, s- and t-butyl, allyloxy, propargyloxy, trifluoromethyl, trifluoromethoxy, trifluoromethylthio, cyclohexyl, methoxycarbonyl, ethoxycarbonyl, acetyloxy, or phenyl or phenoxy, optionally substituted by fluorine, chlorine or methyl; or represents the radical R—O—N=CH—, wherein R in each case represents methyl, ethyl, n- or i-propyl, n-, i-, s- or t-butyl, allyl or propargyl;

and wherein, in all the radicals shown above by way of their formulae,

X', in each case represents oxygen or sulphur, n represents 0 or 1 and m likewise represents 0 or 1, $R^2$ represents hydrogen or methyl, $R^3$ represents methyl, ethyl or n- or i-propyl and $R^4$ represents methyl, ethyl, n- or i-propyl, n-, i-, s- or t-butyl, neopentyl, allyl, 2-butenyl, 3-methyl-2-butenyl or propargyl, or represents benzyl which is optionally mono-, di- or tri-substituted by identical or different substituents from the group comprising fluorine, chlorine, methyl and trifluoromethyl, or $R^3$ and $R^4$, together with the nitrogen atom to which they are bonded, represent 1-pyrrolidinyl, 1-piperidinyl, 1-piperazinyl, 4-morpholinyl or 1-perhydroazepinyl, in each case optionally mono-, di- or tri-substituted by identical or different substituents, substituents which may be mentioned being: methyl, ethyl, n- or i-propyl, phenyl, hydroxymethyl, acetyloxymethyl, methoxycarbonyloxymethyl, dimethylaminocarbonyloxymethyl, diethylaminocarbonyloxymethyl or methoxyacetyloxymethyl.

excluding the compound in which $R^3$ and $R^4$ represent methyl, $R^1$ represents substituted phenyl and $R^2$ at the same time represents hydrogen.

The following compounds of the general formula (I) may be mentioned specifically in addition to the compounds mentioned in the preparation examples:
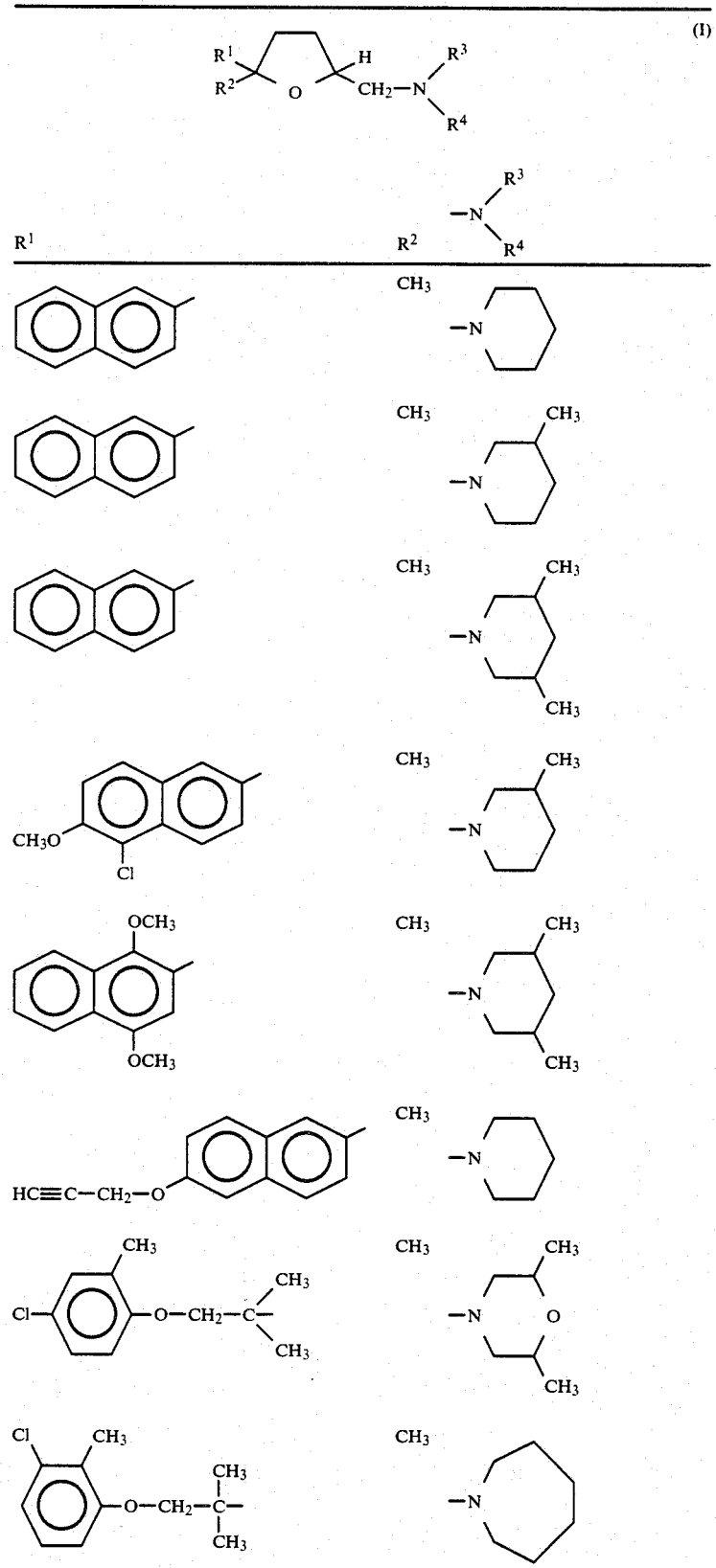

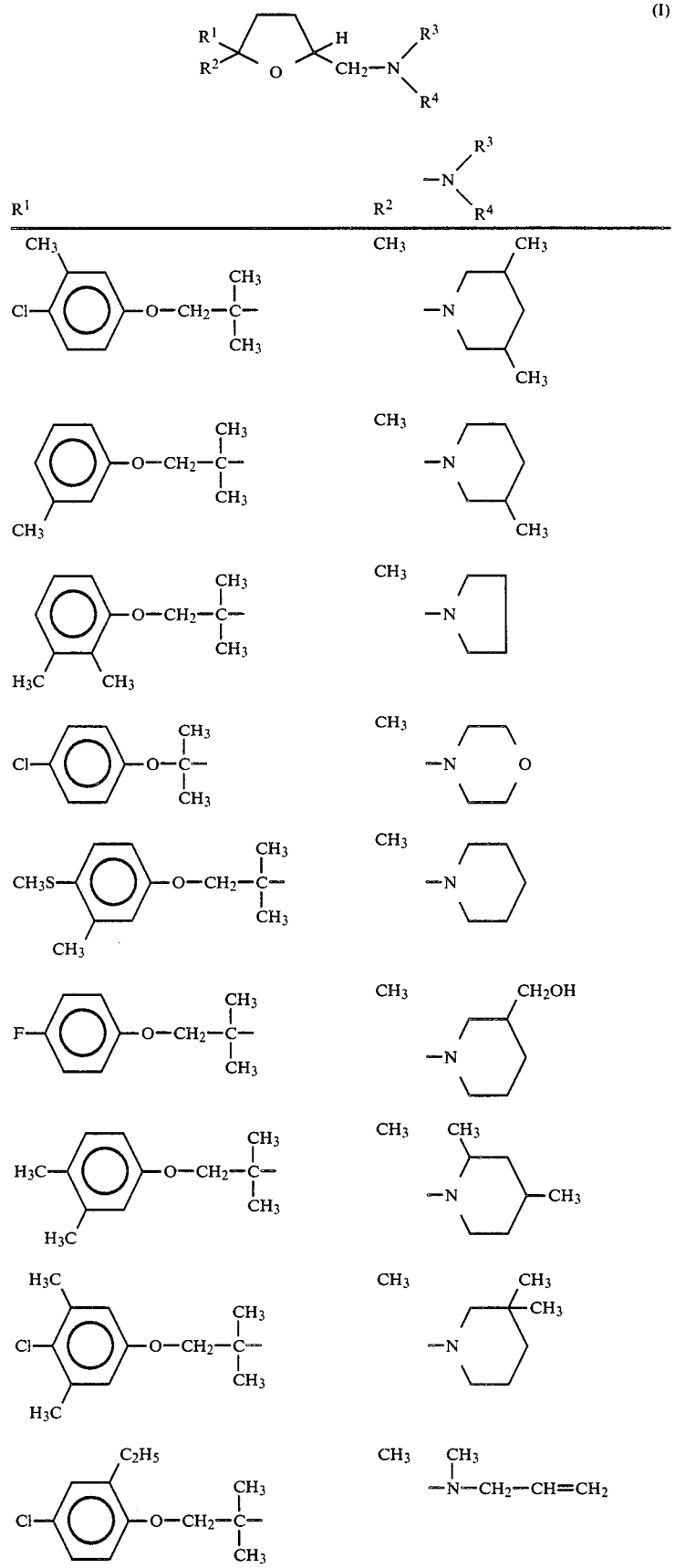

-continued
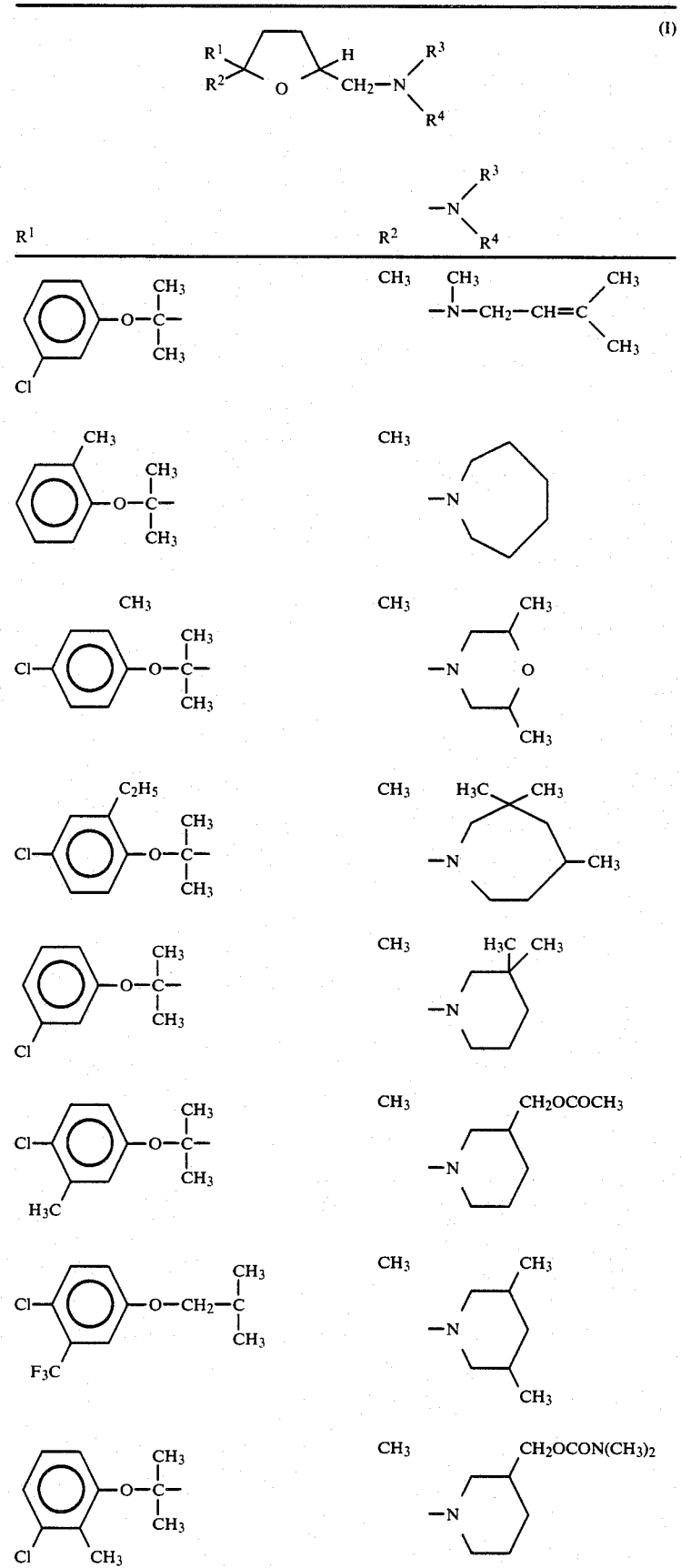

-continued
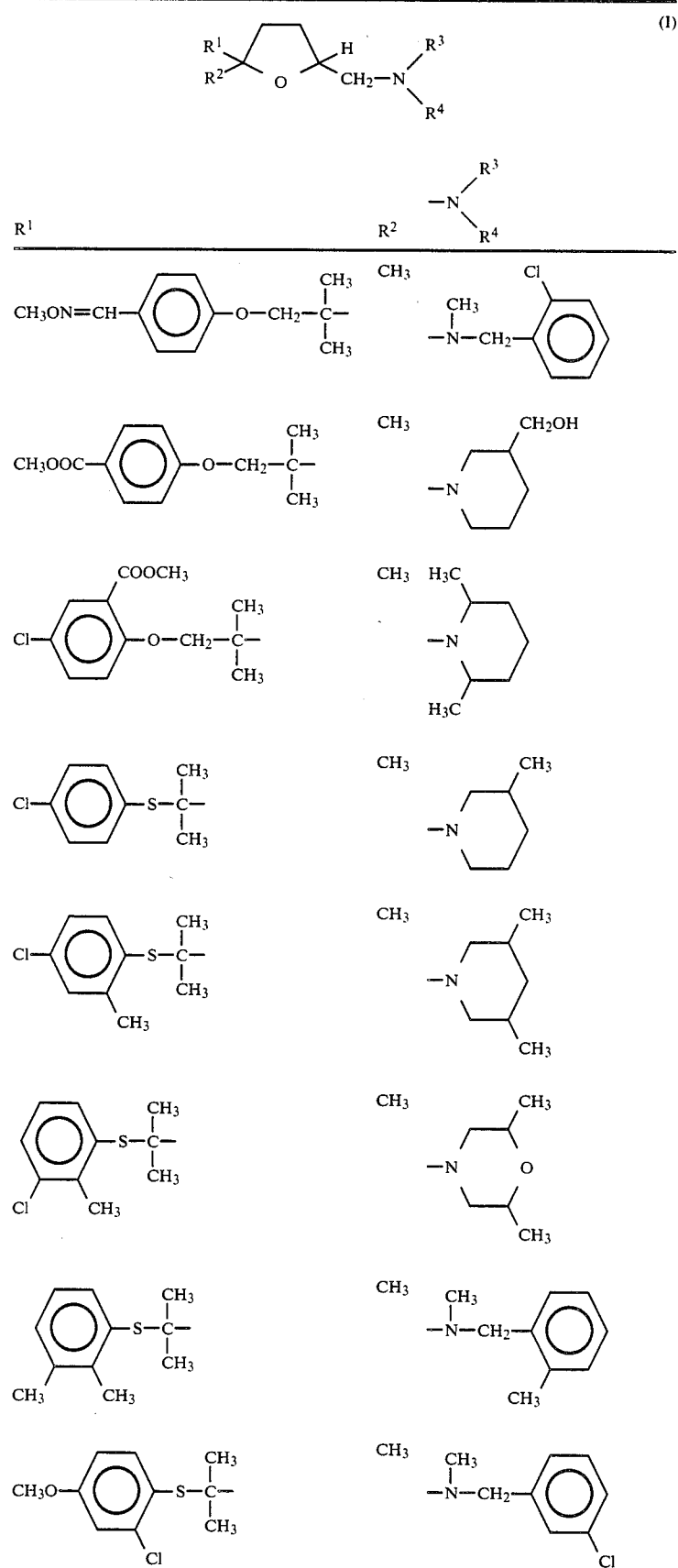

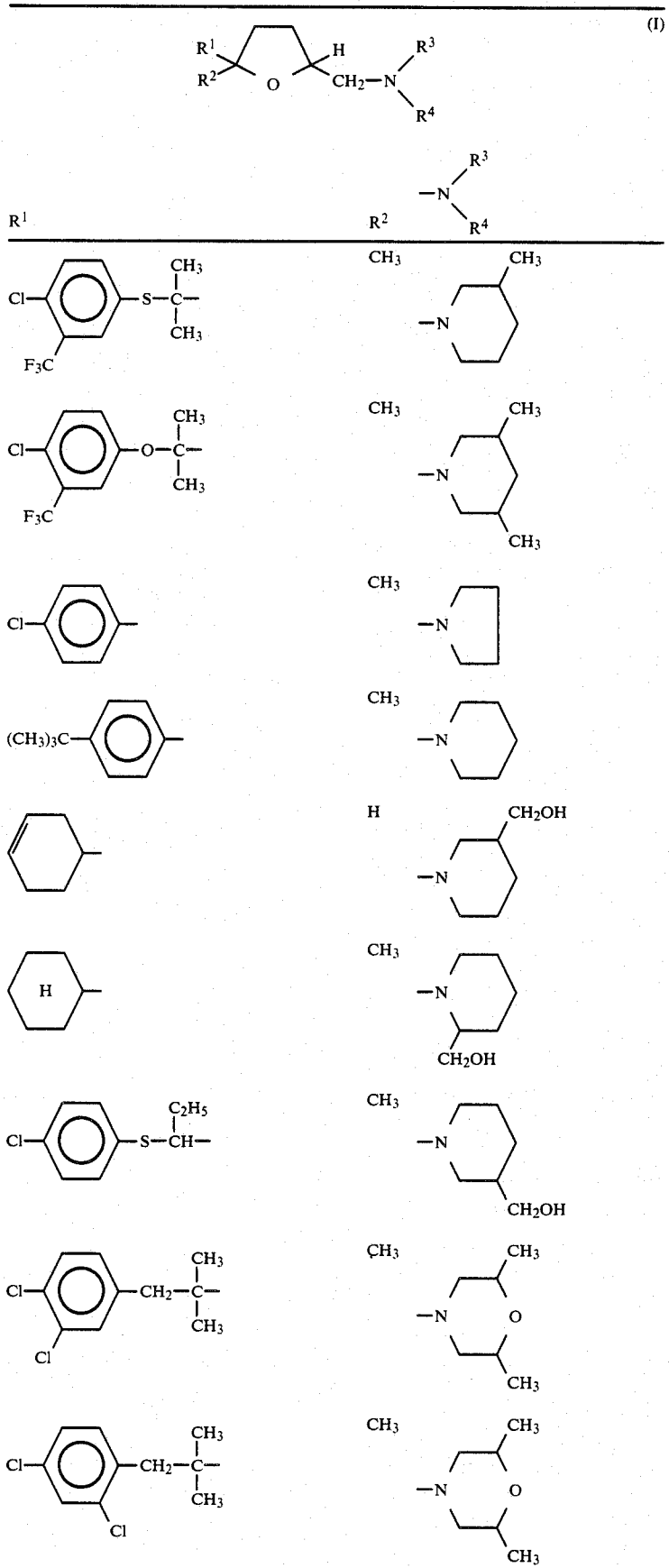

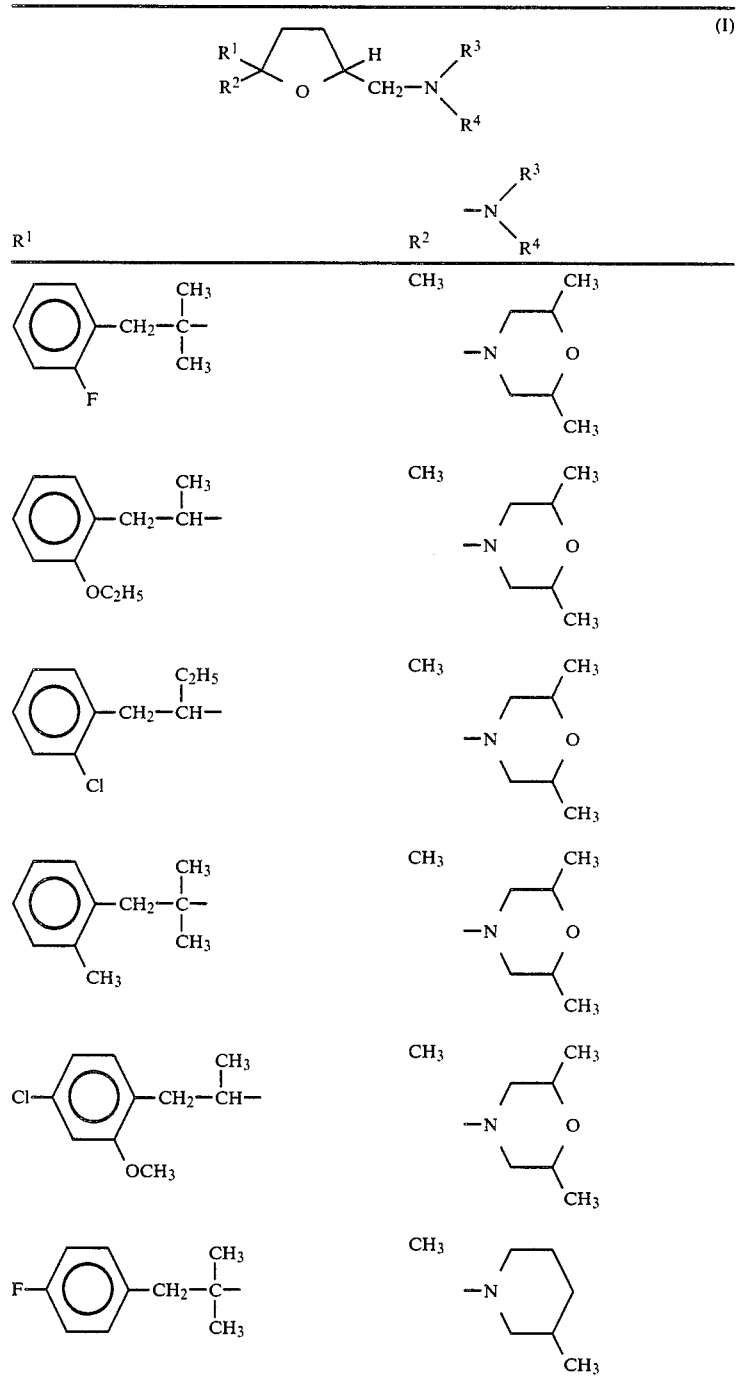
If, for example, 2-bromomethyl-5-(4-chlorophenyl)-tetrahydrofuran and 3,5-dimethylpiperidine are used as starting substances, the course of the reaction in the process according to the invention cn be represented by the following equation:
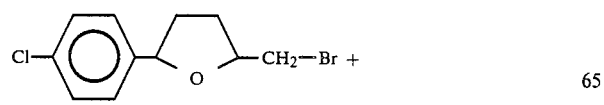
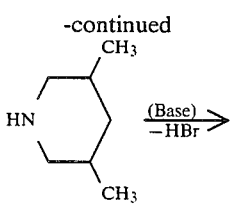

-continued

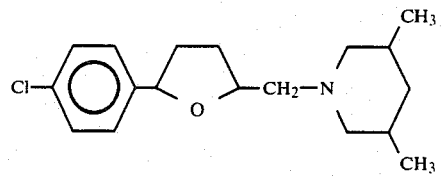

Formula (II) provides a general definition of the tetrahydrofuran derivatives required as starting substances for carrying out the process according to the invention. In this formula (II), $R^1$ and $R^2$ preferably represent those substituents which have already been mentioned as preferred for these radicals in the description of the substances of the formula (I).

X preferably represents halogen, in particular chlorine, bromine or iodine, or represents optionally substituted alkylsulphonyloxy, alkoxysulphonyloxy or arylsulphonyloxy, in particularly methanesulphonyloxy, methoxysulphonyloxy, trifluoromethanesulphonyloxy or p-toluenesulphonyloxy.

Some of the tetrahydrofuran derivatives of the formula (II) are known (compare, for example, EP-OS (European Published Specification) No. 68,331). They are obtained, for example, when alkenylcarbinols of the formula (IV)

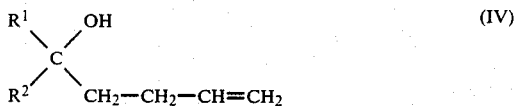

in which
$R^1$ and $R^2$ have the above mentioned meaning, are reacted with halogen, such as, for example, bromine or iodine, if appropriate in the presence of a diluent, such as, for example, diethyl ether, and if appropriate in the presence of a catalyst or an acid-binding agent, such as potassium iodide, quinoline or potassium carbonate, at temperatures between +20° C. and 120° C. (compare, for example, Houben-Weyl "Methoden der organischen Chemie" ("Methods of organic chemistry"), volume VI/3, page 537, 4th edition, Thieme Verlag Stuttgart; and Ukr. Khim. Zh. 48, 72–76 (1982)), or when trihydroxy compounds of the formula (V)

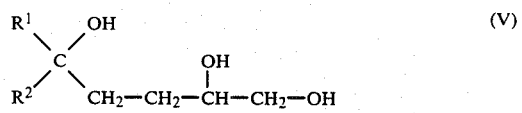

in which
$R^1$ and $R^2$ have the abovementioned meaning, are cyclized with acids, such as, for example, sulphuric acid or phosphonic acid, in the customary manner (compare, for example, Houben-Weyl "Methoden der organischen Chemie" ("Methods of organic chemistry"), volume VI/3 page 528; 4th edition, Thieme Verlag Stuttgart or Khim. Geterotsikl. Soedin. Sb. No. 2, 15–17, [1970] or C.A. 77, 48114 g), and the hydroxymethyltetrahydrofurans thus obtainable, of the formula (VI)

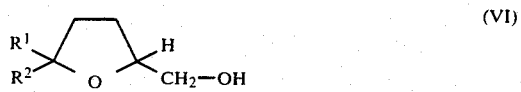

in which
$R^1$ and $R^2$ have the abovementioned meaning, are reacted in a 2nd stage with, for example, sulphonic acid halides of the formula (VII)

in which
$R^5$ represents optionally substituted alkyl, alkoxy or aryl, in particular methyl, methoxy, trifluoromethyl or p-tolyl, and Hal represents halogen, in particular chlorine or bromine, if appropriate in the presence of a diluent, such as, for example, methylene chloride, and if appropriate in the presence of an acid-binding agent, such as, for example, pyridine, at temperatures between 0° C. and +120° C.

The alkylcarbinols of the formula (IV) and the trihydroxy compounds of the formula (VI) are known, or they can be prepared by known processes, in a simple analogous manner (compare, for example, Bull. Soc. Chim. France 1967, 2466–2472, Helvetica. Chim. Acta 64, 2606–2613 [1981], and Tetrahedron Lett. 22, 4995–4998 [1981]).

The sulphonic acid halides of the formula (VII) are generally known compounds of organic chemistry.

Formula (III) provides a general definition of the amines also required as starting substances for carrying out the process according to the invention. In this formula (III), $R^3$ and $R^4$ preferably represent those radicals which have already been mentioned as preferred for these substituents in the description of the substances of the formula (I) according to the invention.

The amines of the formula (III) are generally known compounds of organic chemistry.

Possible diluents for carrying out the process according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride; ethers, such as dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate, or sulphoxides, such as dimethyl sulphoxide.

If appropriate, the process according to the invention can be carried out in the presence of an acid-binding agent.

Possible acid-binding agents are all the usual inorganic or organic bases. These include, for example, alkali metal hydroxides, such as sodium hydroxide or potassium hydroxide; alkali metal carbonates, such as sodium carbonate, potassium carbonate or sodium bicarbonate; and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU). It is also possible for the amine of the formula (III) employed as the particular reactant to be used in an appropriate excess as the acid-binding agent.

If appropriate, the process according to the invention is carried out in the presence of a catalyst. Alkali metal iodides, such as, for example, potassium iodide, are preferably used.

The reaction temperatures can be varied within a substantial range in carrying out the process according to the invention. In general, the reaction is carried out at temperatures between +20° C. and +250° C., preferably at temperatures between +50° C. and +200° C.

The process according to the invention can be carried out under normal pressure or under increased pressure. Under pressure, the reaction is in general carried out under between about 1.5 atmospheres gauge and 5 atmospheres gauge preferably between 1.5 atmospheres gauge and 3 atmospheres gauge.

In carrying out the process according to the invention, in general 1 to 30 moles, preferably 1 to 15 moles, of amine of the formula (III) and, if appropriate, 1 to 5 moles of acid-binding agent and, if appropriate, 0.01 to 0.5 mole of catalyst are employed per mole of tetrahydrofuran derivative of the formula (II).

The end products of the formula (I) are worked up and isolated by generally customary processes.

The following acids can preferably be used for the preparation of acid addition salts of the formula (I) which are tolerated by plants: the hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example, by filtration, and if appropriate purified by washing with an inert organic solvent.

Salts of metals of main groups II to IV and of subgroups I and II and IV to VIII can preferably be used for the preparation of metal salt complexes of the compounds of the formula (I), examples of metals which may be mentioned being copper, zinc, manganese, magnesium, tin, iron and nickel.

Possible anions of salts are those which, preferably, are derived from the following acids: the hydrogen halide acids, such as, for example, hydrochloric acid and hydrobromic acid, and furthermore phosphoric acid, nitric acid and sulphuric acid.

The metal salt complexes of compounds of the formula (I) can be obtained in a simple manner by customary processes, thus, for example, by dissolving the metal salt in alcohol, for example ethanol, and adding the solution to a compound of the formula (I). The metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which fall under the generic terms listed may be mentioned as examples, but not by way of limitation: Botrytis species, such as, for example, *Botrytis cinera;* Plasmopara species, such as, for example, *Plasmopara viticola;* Uromyces species, such as, for example, *Uromyces appendiculatus;* Sphaerotheca species, such as, for example, *Sphaerotheca fuliginea,* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita; Fusarium species, such as, for example, Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Pyricularia species, such as, for example, *Pyricularia oryzae;* Pellicularia species, such as, for example, *Pellicularia sasakii;* Pyrenophora species, such as, for example, *Pyrenophora teres* (Conidia form: Frechslera, Syn: Helminthosporium) Cochliobolus species; such as, for example, *Cochliobolus sativus* (Condida form: Frechslera, Syn: Helminthosporium) and Cercospora species, such as, for example, *Cercospora canescens.*

The good toleration, by plants, of the active compounds at the concentrations required for combating plant diseases permits treatment of above-ground parts of plants, of vegetative propagation stock and seeds, and of the soil.

The active compounds according to the invention can be used with particularly good success for combating cereal diseases, such as, for example, against the brown rust of wheat causative organism (*Puccinia recondita*), against the leaf spot of wheat causative organism (*Septoria nodorum*), against the net blotch disease of barley causative organism (*Pyrenophora teres*) or against powdery mildew organisms, for combating rice diseases, such as, for example, against the rice spot disease causative organism (*Pyricularia oryzae*), or for combating vegetable diseases, such as, for example, against the brown rot of tomato causative organism (*Phytophthora infestans*). Besides an outstanding protective activity, they also exhibit very good systemic properties and an in vitro activity in the agar plate test.

The active compounds according to the invention also engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible for example, to increase the content of sugar in sugar beet, sugar cane, pineapples and citrus fruit or to increase the protein content in soy beans or cereals. Using growth regulators it is also possible, for example, to inhibit degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by reaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

The following statements apply to the use as fungicides:

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

For use as plant growth regulators, the amounts applied can be varied within a substantial range. In general, 0.01 to 50 kg, preferably 0.05 to 10 kg, of active compound are used per hectare of soil surface.

As regards the time of application, the rule is that the growth regulators are applied within a preferred period of time, the exact definition of which depends on the climatic and vegetative circumstances.

PREPARATION EXAMPLES

EXAMPLE 1

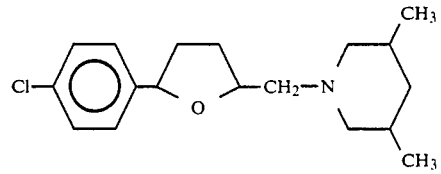

20 g (0.073 mole) of 2-bromomethyl-5-(4-chlorophenyl)-tetrahydrofuran and 25 g (0.22 mole) of 3,5-dimethylpiperidine are heated at 120° C. for 16 hours. The cooled reaction mixture is taken up in ethyl acetate and the mixture is washed twice with water, dried over sodium sulphate and concentrated in vacuo. The oily residue is purified by column chromatography (silica gel 60/ligroin-ethyl acetate 2:1/ethyl acetate). 4.5 g (20% of theory) of 2-(4-chlorophenyl)-5-(3,5-dimethylpiperidin-1-ylmethyl)-tetrahydrofuran are obtained as an oil; $n_D^{20} = 1.5159$.

Preparation of the starting substance

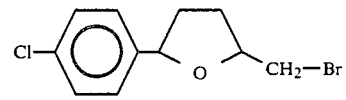

16 g (0.1 mole) of bromine are added dropwise to 17.3 g (0.1 mole) of 5-(4-chlorophenyl)-pent-1-en-5-ol in 50 ml of absolute ether at 0° C. When the addition has ended, 13 g (0.1 mole) of quinoline are added, whereupon the temperature rises to 15° C. and quinoline hydrobromide precipitates. The precipitate is filtered off with suction, the filtrate is evaporated in vacuo and the residue is heated on a waterbath for 1 hour. After cooling, the residue is taken up in ether, the mixture is washed with 15% strength hydrochloric acid and with water, dried over sodium sulphate and concentrated in vacuo and the residue is distilled under a high vacuum. 5 g (18% of theory) of 2-bromomethyl-5-(4-chlorophenyl)tetrahydrofuran of boiling point 145° C./0.13 mbar are obtained.

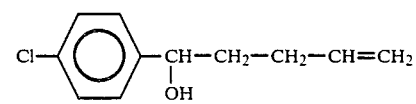

A solution of 70 g (0.5 mole) of 4-chlorobenzaldehyde in 100 ml of absolute ether is added dropwise to a Grignard solution of 12.2 g (0.5 mole) of magnesium and 67.5 g (0.5 mole) of 4-bromo-1-butene in 350 ml of absolute ether, with stirring, and, when the addition has ended, the mixture is heated at the reflux temperature for 2 hours. The cooled reaction mixture is poured into a mixture of 1 liter of saturated ammonium chloride solution and ice, the organic phase is separated off, washed twice with water, dried over sodium sulphate and concentrated in vacuo and the residue is then distilled under a high vacuum. 50 g (58% of theory) of 5-(4-chlorophenyl)-pent-1-en-5-ol of boiling point 100° C.–105° C./0.13 mbar are obtained.

EXAMPLE 2

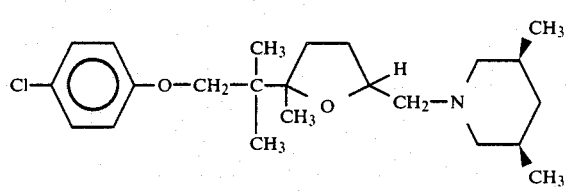

16 g (0.044 mole) of 2-bromomethyl-5-[1-(4-chlorophenoxy)-2-methylprop-2-yl]-5-methyl-tetrahydrofuran are stirred together with 11 g (0.097 mole) of cis-3,5-dimethylpiperidine at a bath temperature of 140° C. for about 14 hours. The resulting reaction mixture is taken up in ether and the mixture is washed several times with water, dried over sodium sulphate and concentrated in vacuo. The oily residue is purified by column chromatography (silica gel 60, ether-petroleum ether 1:1). 7.8 g (45% of theory) of 5-[1-(4-chlorophenoxy)-2-methylprop-2-yl]-2-(cis)-(3,5-dimethylpiperidin-1-ylmethyl)-5-methyl-tetrahydrofuran of refractive index $n_D^{20}$ 1.5049 are obtained.

Preparation of the starting compound

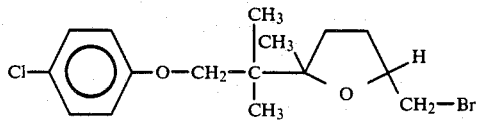

16 g (0.1 mole) of bromine are added dropwise to 28.2 g (0.1 mole) of 7-(4-chlorophenoxy)-5-hydroxy-5,6,6-trimethyl-hept-1-ene in 200 ml of absolute chloroform at room temperature, with stirring, and 13 g (0.1 mole) of quinoline are then added at −10° C., with cooling. The reaction mixture is stirred at room temperature for a further 2 hours and concentrated in vacuo, the residue is taken up in ether, the mixture is filtered, the filtrate is again concentrated in vacuo and the residue is stirred in a waterbath at 95° C. for 1 hour. The resulting mixture is taken up in ether, the mixture is filtered and the filtrate is washed with 15 percent strength hydrochloric acid and then with water, dried over sodium sulphate and freed from the solvent in vacuo. 32.7 g (90% of theory) of 2-bromomethyl-5-[1-(4-chlorophenoxy)-2-methylprop-2-yl]-5-methyl-tetrahydrofuran are obtained as an oil, which can be used in the next stage without further purification.

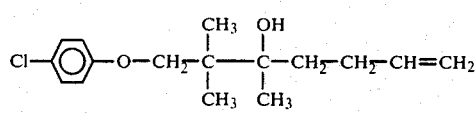

A solution of 48 g (0.2 mole) of 2-[1-(4-chlorophenoxy)-2-methylprop-2-yl]-2-methyl-oxirane in 100 ml of absolute tetrahydrofuran is added dropwise to a Grignard solution of 7.2 g (0.3 mole) of magnesium and 36 g of allyl bromide in 300 ml of absolute ether, while stirring and cooling with ice, and the mixture is heated at the reflux temperature for 4 hours, when the addition has ended, and subsequently stirred at room temperature for a further 15 hours. For working up, the mixture is hydrolysed with aqueous ammonium chloride solution, the organic phase is separated off and dried over sodium sulphate, the solvent is removed in vacuo and the residue is distilled under a high vacuum.

43 g (51% of theory) of 7-(4-chlorophenoxy)-5-hydroxy-5,6,6-trimethyl-hept-1-ene of the boiling point 128° C.–130° C./0.13 mbar are obtained.

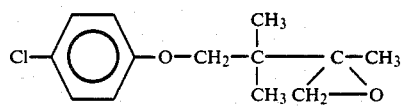

70.2 g (0.33 mole) of sodium methylate are added to a suspension of 72 g (0.33 mole) of trimethylsulphoxonium iodide in 71 g (0.3 mole) of absolute dimethyl sulphoxide in the course of 10 minutes, the mixture is then diluted with 100 ml of absolute tetrahydrofuran and subsequently stirred at room temperature for 3 hours, and 68 g (0.3 mole) of 1-(4-chlorophenoxy)-2,2-dimethyl-butan-3-one in 50 ml of absolute tetrahydrofuran are then added dropwise. When the addition has ended, the mixture is stirred at room temperature for 2 days, the solid which has precipitated is filtered off, the filtrate is concentrated in vacuo, the residue is dissolved in 300 ml of methylene chloride, the solution is washed several times with a total of 200 ml of water and dried over sodium sulfate and the solvent is removed in vacuo. 62 g (86% of theory) of 2-[1-(4-chlorophenoxy)-2-methyl-prop-2-yl]-1-methyl-oxirane are obtained as an oil, which can be employed in the next stage without further purification.

The following compounds of the formula (I) are obtained in a corresponding manner in accordance with the general preparation statements:

$$\begin{array}{c} R^1 \\ R^2 \end{array}\!\!\!\!\underset{O}{\diagdown}\!\!\!\underset{CH_2-N}{\overset{H}{\diagup}}\!\!\!\underset{R^4}{\overset{R^3}{\diagup}} \qquad (I)$$

| Example No. | R¹ | R² | —N(R³)(R⁴) | Physical properties |
|---|---|---|---|---|
| 3. | 4-Cl-C₆H₄-O-CH₂-C(CH₃)₂- | CH₃ | cis-2,6-dimethylmorpholino | $n_D^{20}$ 1.5059 (cis Form) |
| 4. | 2,4-Cl₂-C₆H₃-O-CH₂-C(CH₃)₂- | CH₃ | 3-methylpiperidino | $n_D^{20}$ 1.5114 |
| 5. | 3-Cl-C₆H₄-O-CH₂-C(CH₃)₂- | CH₃ | cis-3,5-dimethylpiperidino | $n_D^{20}$ 1.5389 (cis Form) |
| 6. | 3-Cl-C₆H₄-O-CH₂-C(CH₃)₂- | CH₃ | 3-methylpiperidino | $n_D^{20}$ 1.5374 |
| 7. | 2,4-Cl₂-C₆H₃-O-CH₂-C(CH₃)₂- | CH₃ | cis-3,5-dimethylpiperidino | $n_D^{20}$ 1.5129 (cis Form) |
| 8. | 3,4-Cl₂-C₆H₃-O-CH₂-C(CH₃)₂- | CH₃ | cis-2,6-dimethylmorpholino | $n_D^{20}$ 1.5140 (cis-Form) |
| 9. | 4-F-C₆H₄-O-CH₂-C(CH₃)₂- | CH₃ | piperidino | $n_D^{20}$ 1.4961 |
| 10. | 4-F-C₆H₄-O-CH₂-C(CH₃)₂- | CH₃ | cis-3,5-dimethylpiperidino | $n_D^{20}$ 1.4890 (cis-Form) |

-continued
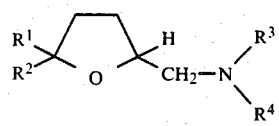 (I)
| Example No. | R¹ | R² |  −N(R³)(R⁴) | Physical properties |
|---|---|---|---|---|
| 11. | 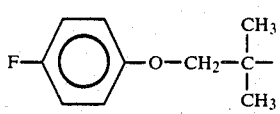 | CH₃ | 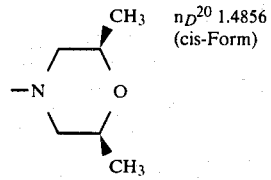 | $n_D^{20}$ 1.4856 (cis-Form) |
| 12. | 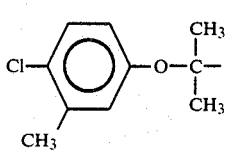 | CH₃ | 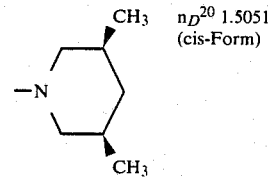 | $n_D^{20}$ 1.5051 (cis-Form) |
| 13. | 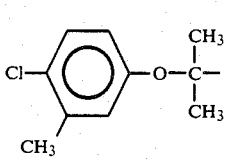 | CH₃ | 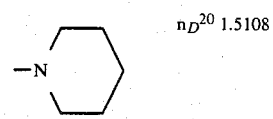 | $n_D^{20}$ 1.5108 |
| 14. | 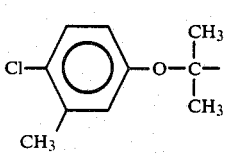 | CH₃ | 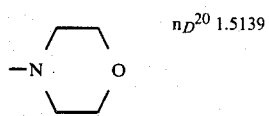 | $n_D^{20}$ 1.5139 |
| 15. | 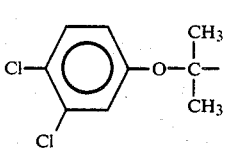 | CH₃ | 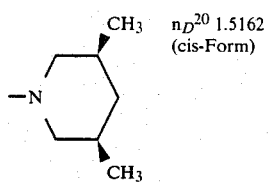 | $n_D^{20}$ 1.5162 (cis-Form) |
| 16. | 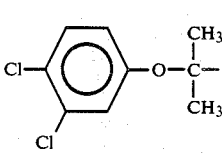 | CH₃ | 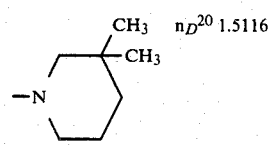 | $n_D^{20}$ 1.5116 |
| 17. | 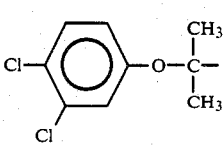 | CH₃ | 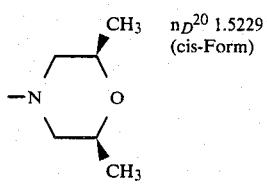 | $n_D^{20}$ 1.5229 (cis-Form) |
USE EXAMPLES
The compounds shown below are employed as comparison substances in the use examples which follow:

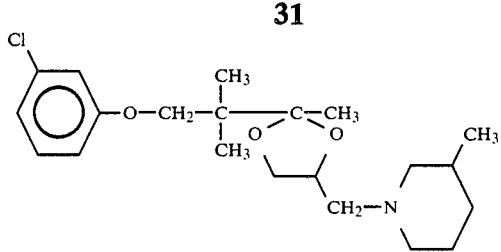

2-[1-(3-Chlorophenoxy)-2-methylprop-2-yl]-2-methyl-4-(3-methylpiperidin-1-ylmethyl)-1,3-dioxolane

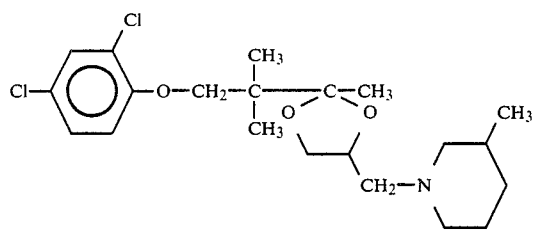

2-[1-(2,4-Dichlorophenoxy)-2-methylprop-2-yl]-2-methyl-4-(3-methylpiperidin-1-ylmethyl)-1,3-dioxolane

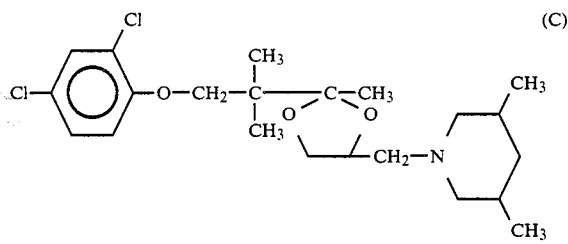

2-[1-(2,4-Dichlorophenoxy)-2-methylprop-2-yl]-2-methyl-4-(3,5-dimethylpiperidin-1-ylmethyl)-1,3-dioxolane (All known from DE-OS (German Published Specification) No. 3,305,769).

EXAMPLE A

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to preparation Examples 4, 5, 6 and 7.

EXAMPLE B

Phytophthora Test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to preparation Examples 1 and 3.

EXAMPLE C

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 2 and 4.

EXAMPLE D

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to preparation Examples 2, 3 and 5.

EXAMPLE E

Influence on growth of sugar-beet
Solvent: 30 parts by weight of dimethylformamide
Emulsifier: 1 part of weight of polyoxyethylene sorbitan monolaurate To produce a suitable preparation of active compound, 1 part by weight of active compound is mixed with the stated amounts of solvent and emulsifier and the mixture is made up to the desired concentration with water.

Sugar-beet is grown in a greenhouse until formation of the cotyledons is complete. In this stage, the plants are sprayed with the preparation of active compound until dripping wet. After 14 days, the additional growth of the plants is measured and the influence on growth in percent is calculated. 0% influence on growth denotes a growth which corresponds to that of the control plants. Negative values characterise an inhibition of growth in comparison to the control plants, while positive values characterize a promotion of growth in comparison to the control plants.

In this test, a distinct activity is shown, for example, by the compound according to preparation Example 1.

It will be understood that the specification and examples are illustrative but not limitative of the present invention and that other embodiments within the spirit and scope of the invention will suggest themselves to those skilled in the art.

We claim:

1. A tetrahydrofuran-2-ylemthylamine of the formula

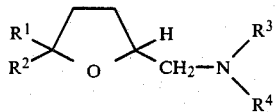

in which $R^1$ represents naphthyl which is optionally mono-, di- or tri-substituted by identical or different substituents selected from fluorine, chlorine, bromine, hydroxy, methyl, ethyl, methoxy, ethoxy, allyloxy, propargyloxy and acetoxy; or represents cycloalkyl or cycloalkenyl with 5 to 7 carbon atoms and in each case optionally mono-, di- or tri-substituted by identical or different substituents selected from methyl and ethyl, or represents phenyl which is optionally mono-, di or tri-substituted by identical or different substituents; or represents a radical of the formula

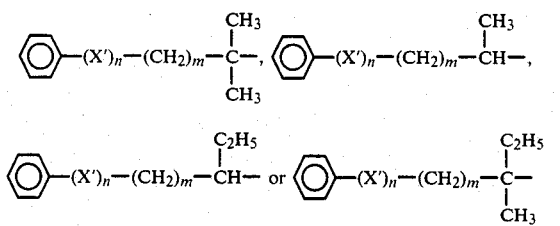

which is optionally mono-, di- or tri-substituted in the phenyl nucleus by identical or different substituents the substituents on the phenyl in each case being selected from hydroxy, fluorine, chlorine, bromine, cyano, nitro, methyl, methoxy, methylthio, ethyl, ethoxy, ethylthio, n- and i-propyl, isopropyloxy, n-,i-,s- and t-butyl, allyloxy, propargyloxy, trifluoromethyl, trifluoromethoxy, trifluoromethylthio, cyclohexyl, methoxycarbonyl, ethoxycarbonyl, acetyloxy, or phenyl or phenoxy, optionally substituted by fluorine, chlorine or methyl; or represents the radical R—O—N=CH—, wherein R in each case represents methyl, ethyl, n- or i-propyl, n-, i-, s- or t-butyl, allyl or propargyl, and wherein, in all the radicals shown above by way of their formulae, X' in each case represents oxygen or sulphur, n represents 0 when m represents 1, and n represents 1 when m represents 0 or 1, $R^2$ represents hydrogen or methyl, $R^3$ represents straight-chain or branched alkyl with 1 to 4 carbon atoms and $R^4$ represents straight-chain or branched alkyl with 1 to 6 carbon atoms, or represents straight-chain or branched alkenyl or alkinyl with in each case up to 6 carbon atoms, or represents aralkyl which has 1 or 2 carbon atoms in the alkyl part and 6 to 10 carbon atoms in the aryl part and is optionally monosubstituted or polysubstituted by identical or different substituents, substituents on the aryl in each case being selected from halogen, straight-chain or branched alkyl with 1 to 4 carbon atoms or halogenoalkyl with 1 or 2 carbon atoms and 1 to 5 identical or different halogen atoms, or $R^3$ and $R^4$, together with the nitrogen atom to which they are bonded, represent a 5-membered to 7-membered saturated heterocyclic radical which has 1 to 3 hetero-atoms, and is optionally monosubstituted or polysubstituted by identical or different substituents, selected from straight-chain or branched alkyl with 1 to 4 carbon atoms, straight-chain or branched alkoxycarbonyl with up to 5 carbon atoms, phenyl, hydroxymethyl or the R'—CO—O—CH$_2$ group, wherein R' represents straight-chain or branched alkyl, alkoxy or alkylamino or dialkylamino with in each case 1 to 6 carbon atoms in the individual alkyl part, or represents straight-chain or branched alkoxyalkyl with in each case 1 to 6 carbon atoms in the two alkyl parts, excluding the compound in which $R^3$ and $R^4$ both represent methyl, $R^1$ represents unsubstituted phenyl and $R^2$ at the same time represents hydrogen.

2. A compound or addition product according to claim 1, in which $R^2$ represents hydrogen or methyl, $R^3$ represents methyl, ethyl or n- or i-propyl and $R^4$ represents methyl, ethyl, n- or i-propyl, n-, i-, s- or t-butyl, neopentyl, allyl, 2-butenyl, 3-methyl-2-butenyl or propargyl, or represents benzyl which is optionally mono-, di- or tri-substituted by identical or different substituents from the group comprising fluorine, chlorine, methyl and trifluoromethyl, or $R^3$ and $R^4$, together with the nitrogen atom to which they are bonded, represent 1-pyrrolidinyl, 1-piperidinyl, 1-piperazinyl, 4-morpholinyl or 1-perhydroazepinyl, in each case optionally mono-, di- or tri-substituted by identical or different substituents, substituents which may be mentioned being: methyl, ethyl, n- or i-propyl, propyl, phenyl, hydroxymethyl, acetyloxymethyl, methoxycarbonyloxymethyl, dimethylaminocarbonyloxymethyl, diethylaminocarbonyloxymethyl or methoxyacetyloxymethyl, excluding the compound in which $R^3$ and $R^4$ both represent methyl, $R^1$ represents unsubstituted phenyl and $R^2$ at the same time represents hydrogen.

3. A compound according to claim 1, wherein such compound is 2-(4-chlorophenyl)-5-(3,5-dimethylpiperidin-1-ylmethyl)-tetrahydrofuran of the formula

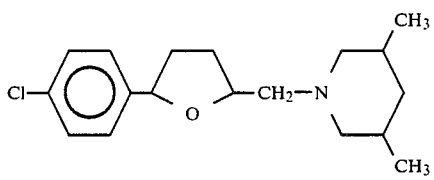

or a plant-tolerated addition product thereof with an acid or metal salt.

4. A compound according to claim 1, wherein such compound is 5-[1-(4-chlorophenoxy)-2-methyl-prop-2-yl]-2-(3,5-dimethylpiperidin-1-ylmethyl)-5-methyl-tetrahydrofuran of the formula

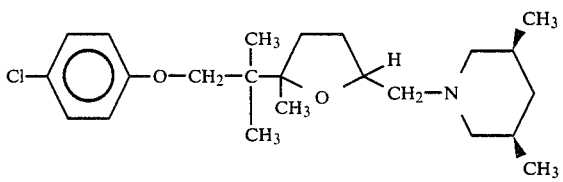

or a plant-tolerated addition product thereof with an acid or metal salt.

5. A compound according to claim 1, wherein such compound is 5-[1-(4-chlorophenoxy)-2-methyl-prop-2-yl]-2-(3,5-dimethylmorpholin-4-ylmethyl)-5-methyl-tetrahydrofuran of the formula

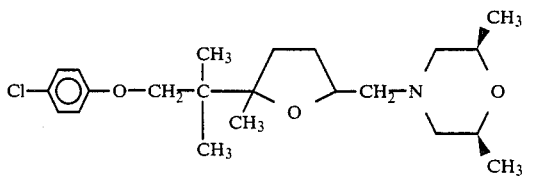

or a plant-tolerated addition product thereof with an acid or metal salt.

6. A compound according to claim 1, wherein such compound is 5-[1-(2,4-dichlorophenoxy)-2-methyl-prop-2-yl]-2-(3-methylpiperidin-1-ylmethyl)-5-methyl-tetrahydrofuran of the formula

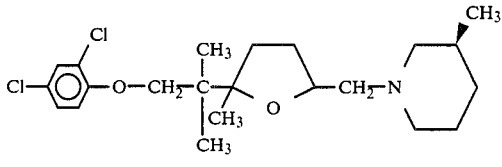

or a plant-tolerated addition product thereof with an acid or metal salt.

7. A compound according to claim 1, wherein such compound is 5-[1-(3-chlorophenoxy)-2-methyl-prop-2-yl]-2-(3,5-dimethylpiperidin-1-ylmethyl)-5-methyl-tetrahydrofuran of the formula

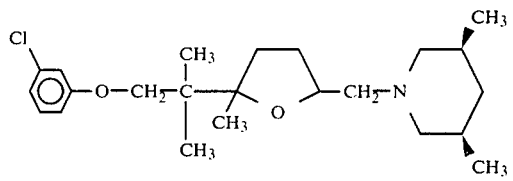

or a plant-tolerated addition product thereof with an acid or metal salt.

8. A compound according to claim 1, wherein such compound is 5-[1-(2,4-dichlorophenoxy)-2-methyl-prop-2-yl]-2-(3,5-dimethylpiperidin-1-ylmethyl)-5-methyl-tetrahydrofuran of the formula

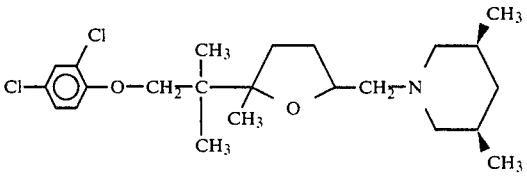

or a plant-tolerated addition product thereof with an acid or metal salt.

9. A fungicidal and plant growth regulating composition comprising a fungicidally or plant growth regulating effective amount of a compound or addition product according to claim 1 in admixture with a diluent.

10. A method of combating fungi which comprises applying to such fungi or to a fungus habitat a fungicidally effective amount of a compound or addition product according to claim 1.

11. The method according to claim 10, wherein such compound is
2-(4-chlorophenyl)-5-(3,5-dimethylpiperidin-1-ylmethyl)-tetrahydrofuran,
5-[1-(4-chlorophenoxy)-2-methyl-prop-2-yl]-2-(3,5-dimethylpiperidin-1-ylmethyl)-5-methyltetrahydrofuran,
5-[1-(4-chlorophenoxy)-2-methyl-prop-2-yl]-2-(3,5-dimethylmorpholin-4-ylmethyl)-5-methyltetrahydrofuran,
5-[1-(2,4-dichlorophenoxy)-2-methyl-prop-2-yl]-2-(3-methylpiperidin-1-ylmethyl)-5-methyltetrahydrofuran,
5-[1-(3-chlorophenoxy)-2-methyl-prop-2-yl]-2-(3,5-dimethylpiperidin-1-ylmethyl)-5-methyltetrahydrofuran or
5-[1-(2,4-dichlorophenoxy)-2-methyl-prop-2-yl]-2-(3,5-dimethylpiperidin-1-ylmethyl)-5-methyltetrahydrofuran,
or a plant-tolerated addition product thereof with an acid or metal salt.

12. A method of regulating the growth of plants which comprises applying to such plants or to a locus in which such plants are to be grown a plant growth-regulating effective amount of a compound or addition product according to claim 1.

13. The method according to claim 12, wherein such compound is
2-(4-chlorophenyl)-5-(3,5-dimethylpiperidin-1-ylmethyl)-tetrahydrofuran, 5-[1-(4-chlorophenoxy)-2-methyl-prop-2-yl]-2-(3,5-dimethylpiperidin-1-ylmethyl)-5-methyltetrahydrofuran, 5-[1-(4-chlorophenoxy)-2-methyl-prop-2-yl]-2-(3,5-dimethylmorpholin-4-ylmethyl)-5-methyltetrahydrofuran, 5-[1-(2,4-dichlorophenoxy)-2-methyl-prop-2-yl]-2-(3-methylpiperidin-1-ylmethyl)-5-methyltetrahydrofuran, 5-[1-(3-chlorophenoxy)-2-methyl-prop-2-yl]-2-(3,5-dimethylpiperidin-1-ylmethyl)-5-methyltetrahydrofuran or 5-[1-(2,4-dichlorophenoxy)-2-methyl-prop-2-yl]-2-(3,5-dimethylpiperidin-1-ylmethyl)-5-methyltetrahydrofuran, or a plant-tolerated addition product thereof with an acid or metal salt.

* * * * *

UNITED STATES PATENT AND TRADEMARK OFFICE
CERTIFICATE OF CORRECTION

PATENT NO. : 4,615,725
DATED : October 7, 1986
INVENTOR(S) : Joachim Weissmüller, et al.

It is certified that error appears in the above-identified patent and that said Letters Patent are hereby corrected as shown below:

Col. 2, line 13              After "$R^1$" delete "represent" and substitute --represents--

Col. 20, lines 28 and 30     Delete "Frechslera" and substitute --Drechslera--

Col. 20, line 30             Delete "Condida" and substitute --Conidia--

Signed and Sealed this

Seventeenth Day of March, 1987

Attest:

DONALD J. QUIGG

Attesting Officer

Commissioner of Patents and Trademarks